United States Patent
Sipilä et al.

(10) Patent No.: US 7,065,174 B2
(45) Date of Patent: Jun. 20, 2006

(54) MEASUREMENT ARRANGEMENT FOR X-RAY FLUORESENCE ANALYSIS

(75) Inventors: Heikki Johannes Sipilä, Espoo (FI); Riitta Kaijansaari, Helsinki (FI)

(73) Assignee: Oxford Instruments Analytical Oy, Espoo (FI)

( * ) Notice: Subject to any disclaimer, the term of this patent is extended or adjusted under 35 U.S.C. 154(b) by 0 days.

(21) Appl. No.: 10/987,145

(22) Filed: Nov. 12, 2004

(65) Prior Publication Data

US 2005/0129174 A1 Jun. 16, 2005

(30) Foreign Application Priority Data

Dec. 1, 2003 (FI) .................................. 20031753

(51) Int. Cl.
*G01N 23/223* (2006.01)
(52) U.S. Cl. .......................... 378/44; 378/45
(58) Field of Classification Search ............ 378/44–49, 378/83, 88–90, 161, 119, 143
See application file for complete search history.

(56) References Cited

U.S. PATENT DOCUMENTS

| | | | | |
|---|---|---|---|---|
| 3,610,984 A | * | 10/1971 | Seki et al. ................... | 378/125 |
| 4,017,757 A | * | 4/1977 | DeCou, Jr. .................. | 378/124 |
| 4,959,848 A | * | 9/1990 | Parobek ...................... | 378/46 |
| 5,365,563 A | | 11/1994 | Kira et al. | |
| 5,832,054 A | * | 11/1998 | Kuwabara .................... | 378/45 |
| 5,898,752 A | * | 4/1999 | Van Der Wal ................ | 378/49 |
| 5,978,442 A | * | 11/1999 | Kuwabara .................... | 378/46 |
| 5,982,847 A | * | 11/1999 | Nelson ......................... | 378/47 |
| 6,075,839 A | | 6/2000 | Treseder | |
| 6,233,307 B1 | * | 5/2001 | Golenhofen ................. | 378/45 |
| 6,577,704 B1 | | 6/2003 | Holz | |
| 6,668,039 B1 | * | 12/2003 | Shepard et al. .............. | 378/47 |

FOREIGN PATENT DOCUMENTS

| | | |
|---|---|---|
| EP | 1054254 A2 | 11/2000 |
| WO | WO 98/50937 A1 | 11/1998 |
| WO | WO 03/048745 A2 | 6/2003 |

OTHER PUBLICATIONS

Finnish Search Report for Finnish Patent Application No. 20031753.

\* cited by examiner

*Primary Examiner*—Edward J. Glick
*Assistant Examiner*—Irakli Kiknadze
(74) *Attorney, Agent, or Firm*—Wood, Phillips, Katz, Clark & Mortimer (57) ABSTRACT

A portable measurement apparatus is presented for inducing and measuring fluorescent X-ray radiation. It comprises an X-ray source (303, 902, 1005, 1105) adapted to controllably irradiate a sample (301, 803) with X-rays, and a detector (305, 406, 1006, 1106) adapted to detect fluorescent radiation emitted by said sample (301, 803). The X-ray source (303, 902, 1005, 1105) is an X-ray tube, an anode of which comprises at least one of silver, rhodium and molybdenium. Consequently said X-ray tube is adapted to controllably emit L-line radiation of at least one of silver, rhodium and molybdenium.

23 Claims, 6 Drawing Sheets

MEASUREMENT ARRANGEMENT FOR X-RAY FLUORESENCE ANALYSIS

TECHNICAL FIELD

The invention concerns generally the technology of using X-ray fluorescence analysis for analysing the contents of samples. Especially the invention concerns the problem of how should the measurement apparatus be constructed so that the detection of very small impurity concentrations with even relatively soft X-rays would be possible.

BACKGROUND OF THE INVENTION

X-ray fluorescence analysis is a common and widely used tool in analysing the contents of certain elements and/or compounds in given samples. As a first example we will consider the task of analysing the sulphur content of liquid hydrocarbons, such as petrol (gasoline), diesel oil and other liquid fuels. Environmental considerations have promoted the enactment of relatively tight limits for allowable sulphur content in liquid fuels. A measurement arrangement should be able to reliably measure concentrations in the order of only few ppm (parts per million).

Figure 1:
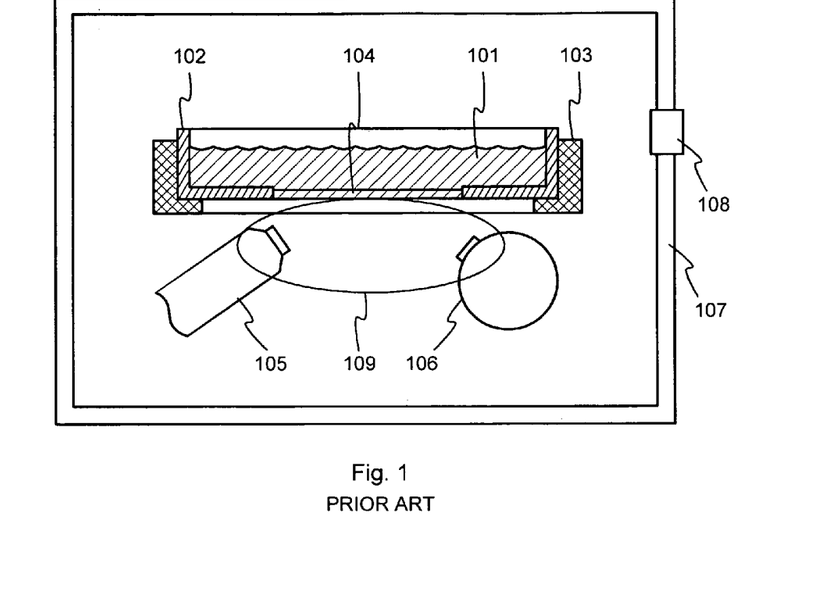
FIG. 1 illustrates a prior art measurement arrangement.

FIG. 1 illustrates schematically a prior art arrangement for measuring the sulphur content of a liquid fuel sample through X-ray fluorescence analysis. The sample 101 is poured into container, which in this arrangement is a cup 102 supported in a holder 103. The bottom of the cup 102 comprises a window 104 for X-rays to pass through. An X-ray tube 105 or some other suitable source of X-rays is used to irradiate the sample 101 through the window 104. Fluorescent X-ray quanta from the sample 101 are collected and counted in a detector 106. The whole arrangement is located in an enclosure 107 that comprises a valve 108 for flushing the measurement arrangement with a suitable protective gas, such as helium or nitrogen.

Sulphur has a fluorescent emission line at approximately 2.3 keV (kiloelectronvolt). Very close to it is a 3 keV fluorescent line of argon. Pure atmospheric air contains around one percent argon, which means that accurate results cannot be obtained using a proportional counter if the space 109 between the X-ray source 105, the window 104 and the detector 106 is filled with air. Flushing the measurement arrangement with hydrogen, helium or nitrogen has been regarded as mandatory to keep air (and thus argon) from interfering with the measurement.

Figure 2:
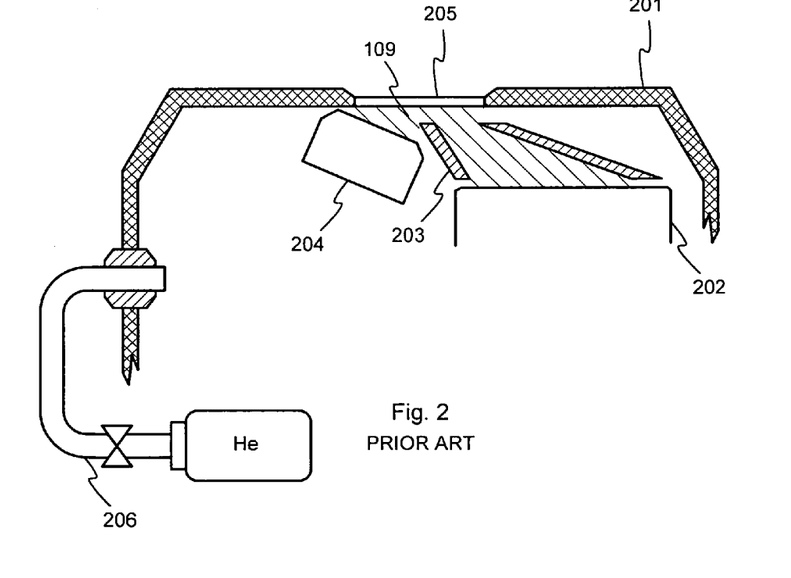
FIG. 2 illustrates another prior art measurement arrangement.

FIG. 2 illustrates a second prior art example, which in this case corresponds to measuring the concentration of certain elements in metal alloys. A measurement head is housed in a gastight enclosure 201 and comprises an X-ray source 202, X-ray directing means 203 and a detector 204. A contact surface (here the top surface) of the enclosure 201 is designed to allow placing the measurement head very close to a metallic sample. A window 205 in said contact surface is permeable to soft X-rays and allows excitation radiation from the X-ray source 202 to pass through to the sample, and fluorescent radiation induced in the sample to enter the measurement head and hit the detector 204. A flushing arrangement 206 comprises means for flushing the inside of the enclosure with a gas, typically hydrogen or helium. The open space 109 within the enclosure 201 between the X-ray source 202, the window 205 and the detector 204 must not contain any substance that would interfere with the measurement.

Detecting elements from metal alloys with an arrangement like that in FIG. 2 typically involves measuring the fluorescent emission lines of aluminium, magnesium or silicon, with energies of 1.49 keV, 1.25 keV and 1.74 keV respectively. The 3 keV line of argon causes little interference with these measurements, but the absorption of the fluorescent radiation in air becomes a problem—hence the need for gas flushing.

The constant need for flushing is a problem, because flushing gases of the required purity are not cheap, because the required settling time before the actual measurement can begin is relatively long and because the gas containers and tubing tend to make the overall appearance of the apparatus somewhat clumsy.

An obvious alternative for flushing the measurement arrangement with a gas would be to produce a vacuum into the relevant space 109. However, concerning the application shown in FIG. 1, liquid hydrocarbons are highly volatile even at normal atmospheric pressure, and exposing them to a vacuum would cause the whole sample to evaporate very quickly. The relative softness (i.e. the low energy level) of the X-rays involved requires the window 104 to be very thin, and made of a material that does not absorb X-rays of the energy involved to any considerable extent. It is not possible to have a vacuum only in space 109 and to have the sample at normal atmospheric pressure, for example by using the construction of FIG. 2 and replacing the flushing arrangement 206 with a vacuum pump, because none of the known window materials could stand the pressure difference.

Eliminating an empty space between the X-ray source, the window and the detector altogether has not been regarded as a feasible solution either. The soft X-rays involved only penetrate the sample to a depth of a few tens of micrometres. The sample surface area that is irradiated and from which fluorescent quanta are collected must have a reasonable size, at least several square millimetres. Direct propagation of X-rays from the X-ray source to the detector must not be possible. All solid materials that could be used to fill the empty space absorb the X-rays too much. All these boundary conditions have precluded the appearance of measurement arrangements with no empty space 109.

Yet another known drawback of the prior art arrangement is the possible change in measurement geometry, caused by creeping deformation of the window. This is a problem especially in the case of FIG. 1. Being made of a polymer, typically polypropylene, and being constantly exposed to hydrocarbon solvents, the window material is prone to stretching. Even if a careful selection of materials could prevent any damage caused by chemical incompatibility, it is possible that a person conducting the measurement uses a too heavy sample or leaves the sample in the cup for an extensively long time, in which case the sheer mechanical load can cause a permanent deformation of the window 104.

SUMMARY OF THE INVENTION

It is an objective of the present invention to provide a measurement arrangement for X-ray fluorescence analysis that does not need flushing with any externally provided gas. Another objective of the invention is to provide a measurement arrangement for the X-ray fluorescence analysis of liquid samples where unintentional changes in measurement geometry can be prevented. A yet other objective of the invention is to provide a measurement apparatus for X-ray fluorescence analysis, which apparatus is small-sized and compact and easily serviceable.

The objectives of the invention are achieved by designing and manufacturing the measurement apparatus so that a measurement head can accept a separate gas-filled enclosure that fills a space between the X-ray source, the sample window and the detector. The objectives of the invention are especially well met if such an enclosure is made to consist of a cassette that can be easily removed for service, replacement and/or measurement operation without a cassette.

A measurement apparatus according to the invention is characterised by the features recited in the characterising part of the independent claim directed to a measurement apparatus.

The invention is also directed to an interface cassette, the characteristic features of which are recited in the independent claim directed to an interface cassette.

According to a first aspect of the invention, instead of flushing the whole measurement arrangement with a gas, it suffices to arrange a gas atmosphere into that part of it where X-rays propagate. In other words, a separate enclosure is provided between the X-ray source, the detector, and the container in which the sample liquid is located. This enclosure contains suitable gas and has windows for X-rays to pass through next to the X-ray source, the detector and the sample container. The window that is next to the sample container also acts as a support for the container wall next to it. Most advantageously the gas in the enclosure is slightly under pressure, causing the window that is next to the sample container to bulge outwards slightly. When the gas enclosure and the sample container come adjacent to each other, the bulging of said window drives all air out from between the gas enclosure and the sample container.

For the purpose of easy replacement and maintenance it is advantageous to make the gas enclosure appear as a separate mechanical entity or "cassette", which is held in place either by simple mechanical attachment means or even by gravity only, so that the cassette is just dropped into place in the measurement apparatus. For measurements in which the surrounding gas atmosphere does not cause significant interference, it is possible to even leave out the cassette.

According to a second aspect of the invention certain structural and operational parameters of the measurement arrangement are selected in a way that optimises portability and easy handling. For example, it appears to be advantageous to select the excitation radiation among the so-called L-lines of an X-ray tube with an anode made of silver, rhodium or molybdenium. The X-ray tube may be of the end window or the side window type. Beryllium of appropriately selected thickness is a preferred choice for various windows in the structure, but can in many cases be replaced with polyimide or polycarbonate. It is also advantageous to use a collimator between the X-ray tube and the sample, and to match the material of the collimator with the anode material of the X-ray tube so that possible fluorescent radiation produced in the collimator material will add the overall intensity of available excitation radiation.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE INVENTION

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

Figure 3:
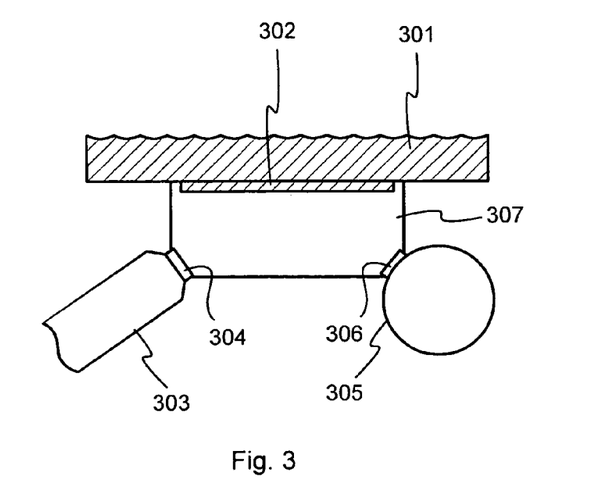
FIG. 3 illustrates the principle of a separate gas enclosure according to an embodiment of the invention.

FIG. 3 illustrates schematically the principle of using a separate gas enclosure according to an embodiment of the invention. For the purpose of performing an X-ray fluorescence analysis, there is a sample 301 of a liquid substance that is to be analysed. A window 302 made of a material substantially transparent to X-rays offers an air-free interface to the sample. For the purpose of unambiguity, the window 302 is here designated as the sample window. The interface being air-free means that considering the spatial region where X-ray illumination and fluorescence takes place, at least a major part of the sample side of the sample window 302 is below the surface of the sample 301, so that between the sample window 302 and the sample substance there is no air.

The arrangement comprises an X-ray source 303 for controllably irradiating the sample 301 with X-rays through the sample window 302. As a part of the X-ray source 303 there is an exit window 304, through which the X-rays come out of the X-ray source. The arrangement comprises also a detector 305 for collecting and detecting fluorescent X-ray quanta that result from the relaxation of excited states in the sample atoms bombarded with the X-rays from the X-ray source 303. An entrance window 306 constitutes an entrance to the detector 305 for the fluorescent X-ray quanta. The exit window 304 and entrance window 306 are naturally transparent to X-rays.

A gas-filled enclosure 307 is located between the X-ray source 303, the detector 305 and the sample 301 so that the following conditions are fulfilled:
  the interfaces between the gas-filled enclosure 307 on one hand and the exit window 304, the entrance window 306 and the sample window 104 on the other hand are substantially air-free; i.e. there is no significant air gap between the gas-filled enclosure 307 and any of said windows, the parts of the walls of the gas-filled enclosure 307 that are next to said windows are transparent to X-rays, so that at least X-rays of the energy involved in the measurement can easily pass in to and out of the gas-filled enclosure at these locations, the gas-filled enclosure 307 is hermetically sealed and contains a gas that does not absorb substantial amounts of X-rays of the energy involved in the measurement or cause fluorescence on energy levels that would interfere with the measurement, and preferably but not mandatorily the pressure of said gas inside the gas-filled enclosure 307 is slightly higher than the ambient pressure outside the gas-filled enclosure, and preferably but not mandatorily the gas-filled enclosure 307 is a single entity mechanically separate from e.g. the X-ray source 105, the detector 106 and any containers used for holding the sample 101, with simple mechanical attachment means for attaching the gas-filled enclosure 307 into place in the measurement arrangement.

Figure 4:
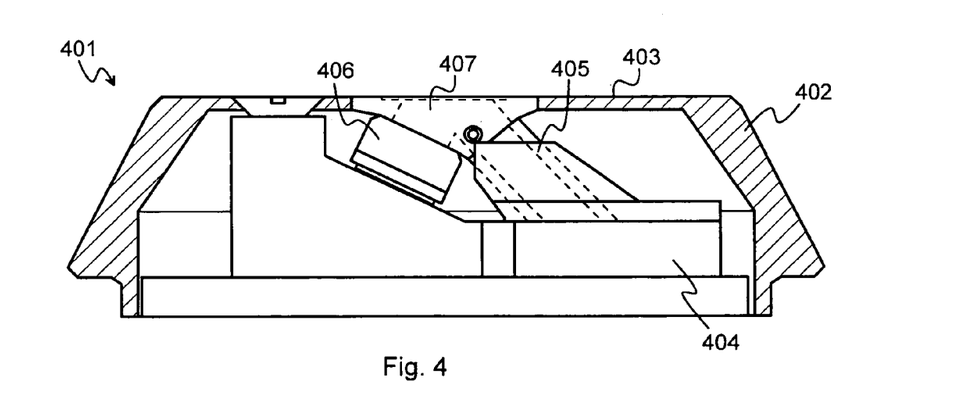
FIG. 4 illustrates a part of a measurement apparatus according to an embodiment of the invention.

FIG. 4 is a partial cross section that illustrates an exemplary practical implementation of the principle shown in FIG. 3. A measurement head 401 comprises an outer cover part 402, one surface of which is adapted to receive and/or to be placed against a sample. Said surface is designated here as the sample receiving surface 403. Inside the outer cover 402 there is a place 404 for an X-ray source, a collimator 405 adapted to direct X-rays from an X-ray source towards the middle of the sample receiving surface 403, and a detector 406 adapted to receive fluorescent radiation from a sample placed against the sample receiving surface 403. The central part of the sample receiving surface 403 defines an opening, within which there is what we designate here as the interface cassette 407.

Mechanically the interface cassette 407 is designed to accurately match the mechanical design of the other parts. When in place, the interface cassette 407 fills the opening in the middle of the sample receiving surface 403 substantially completely. A major part of the interface cassette 407 is inside the measurement head 401, so that an outer surface of the interface cassette 407 coincides accurately with the rest of the sample receiving surface 403 to constitute a smooth, uniform outer surface. Another surface of the interface cassette 407 fits accurately against an X-ray receiving surface of the detector 406. Yet another surface of the interface cassette 407 fits accurately against an exit aperture of the collimator 405.

Figure 5:
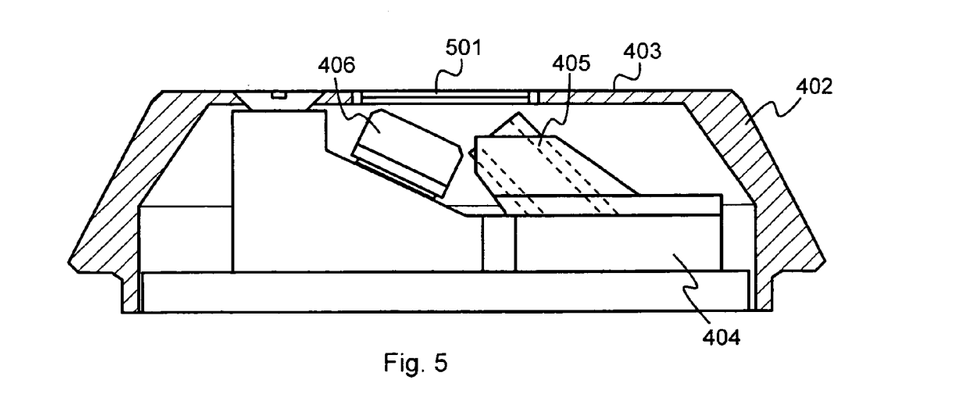
FIG. 5 illustrates a part of a measurement apparatus according to an embodiment of the invention in a different configuration.

FIG. 5 illustrates otherwise the same measurement head but without an interface cassette. In the configuration of FIG. 5, there is instead a protective window 501 that fills essentially completely the opening in the middle of the sample receiving surface 403. An upper surface of the window 501 coincides accurately with the level of the sample receiving surface 403. All other parts 402, 404, 405 and 406 are the same as in FIG. 4. Together the parts 402, 403, 404, 405, 406, 407 and 501 constitute a system for equipping a measurement head alternatively with an interface cassette 407 or with a protective window 501. As such it would be possible to even design an interface cassette so that when in place, an outer surface thereof would remain slightly lower than the level of the sample receiving surface 403, and to cover the interface cassette with an outer protective window like that 501 shown in FIG. 5. However, such an arrangement would introduce unnecessarily many material obstacles along the propagation path of X-rays, and would probably not be very advantageous.

Figure 6:
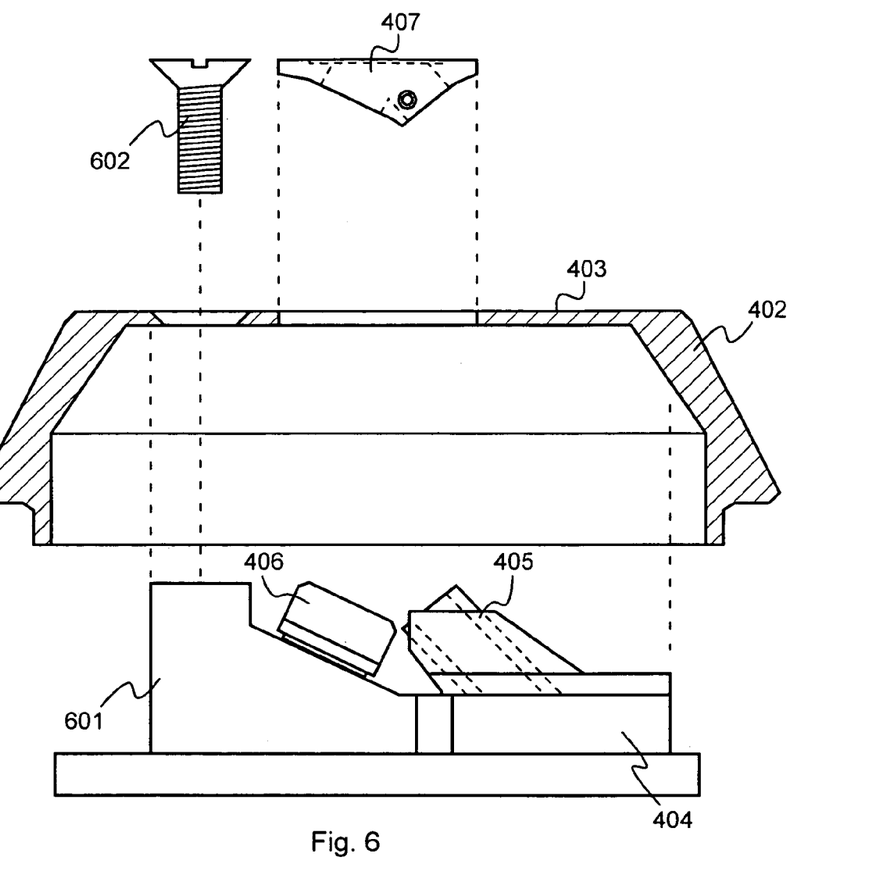
FIG. 6 illustrates the assembly of a part according to FIG. 4.

FIG. 6 illustrates an exemplary way of assembling a measurement head according to FIG. 4. The place 404 for an X-ray source, the collimator 405 and the detector 406 belong to an inner structural entity 601, which has a supporting function. The inner structural entity 601 and the outer cover part 402 are attached together with some mechanical attachment means, of which a bolt 602 is shown as an example. The interface cassette 407 is placed into an opening in the sample receiving surface 403. In the simplest possible case the interface cassette 407 is only dropped in place, but especially for application in portable measurement appliances it is most advantageous to also secure it by using mechanical attachment means, such as bolts, spring-loaded claws or a bayonet lock. If the arrangement involves the option of using a protective window in place of the interface cassette 407, similar attachment considerations apply.

Figure 7:
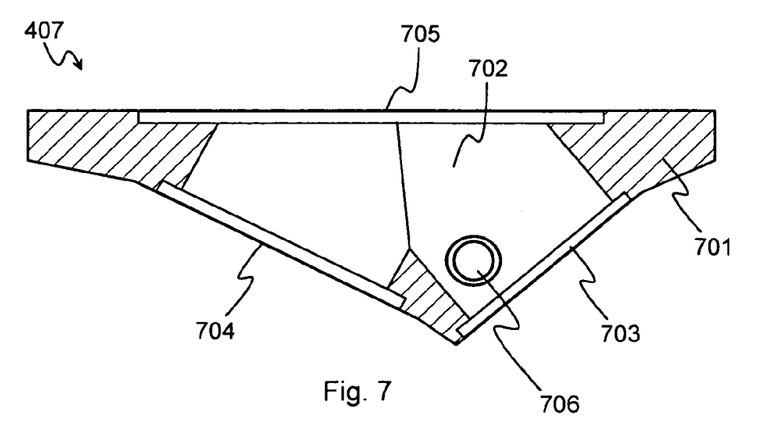
FIG. 7 illustrates an interface cassette according to an embodiment of the invention.

FIG. 7 is a partial cross section of an exemplary interface cassette 407. It comprises a rigid body 701 that mostly determines its outer appearance and mechanical conformity to the other parts of the system. The solid parts of the body 701 define a cavity 702 that has openings to those surfaces of the interface cassette 407 that are to appear against the collimator, against the detector and coincident with the sample receiving surface in an assembled measurement head. Each of these openings has a window to cover it, which makes the cavity 702 hermetically sealed. We will designate these windows as the collimator side window 703, the detector side window 704 and the sample side window 705 of the interface cassette 407.

In order to keep the windows from interfering with the X-rays involved in fluorescence measurements, their material and thickness must be selected so that the windows do not absorb essential amounts of radiation and do not produce fluorescence on energy levels that could be confused with those of a sample to be analysed. Advantageous window materials include but are not limited to beryllium, polyimide (also known as kapton, which is a registered trademark of DuPont corporation) and polycarbonate. A collimator side window 703 made of beryllium should have a thickness between 8 and 50 micrometres. A detector side window 704 made of beryllium should have a thickness between 8 and 25 micrometres. A sample side window 705 made of beryllium should have a thickness between 8 and 25 micrometres; if made of polyimide or polycarbonate the sample side window 705 should have thickness between 0.3 and 5 micrometres.

The cavity 702 contains a gas that absorbs X-rays only weakly and does not produce fluorescence on energy levels that could be confused with those of a sample to be analysed. Typical gases include but are not limited to hydrogen, helium and nitrogen, of which the last-mentioned absorbs more than the others and can be used only with the condition that the X-ray energies involved are higher than approximately 2 keV. It is possible to manufacture the interface cassette up to the stage of hermetically closing the cavity 702 within a gas atmosphere so that no specific gas filling means are needed. However, for most cases it is more practical to make the interface cassette comprise a valve 706 through which the cavity 702 can be flushed with a gas and filled to a desired pressure.

The pressure of the gas inside the interface cassette deserves certain consideration. The surface area of each window 703, 704 and 705 is at least several square millimetres. The thickness of the window material being what it is, it is clear that even relatively small pressure differences between the inside and the outside of the interface cassette tend to make the windows bulge either outwards or inwards, depending on the sign of the pressure difference. If the interface cassette comprises a gas filling valve, it is always possible to control the internal pressure so that before a measurement begins, the internal pressure is set to a desired value, for example that of the ambient pressure. However, it may be advantageous to ensure that the internal pressure of the interface cassette is always slightly higher than ambient pressure.

Figure 8:
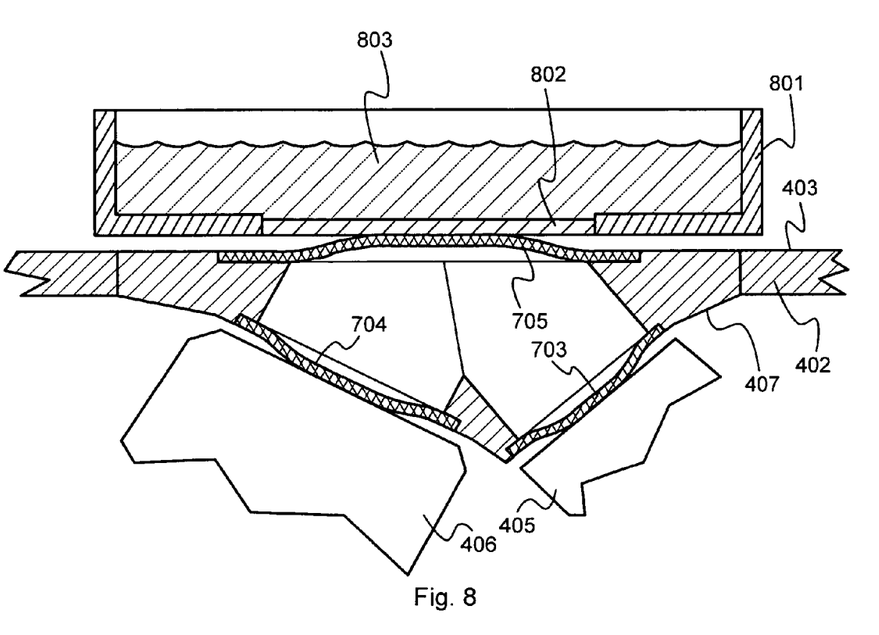
FIG. 8 illustrates a detail of a measurement apparatus according to an embodiment of the invention.

FIG. 8 is a partial cross section that illustrates certain pressure considerations. Here we assume that the X-ray fluorescence analysis involves measuring the sulphur content of a liquid fuel. Analogously with FIG. 4, a measurement head comprises a collimator 405 from which exciting X-rays come out, and a detector 406 to collect fluorescent X-ray quanta. An outer cover part 402 of the measurement head has a sample receiving surface 403 with an opening, and the arrangement comprises an interface cassette 407 within the opening so that an upper external surface of the interface cassette 407 coincides with the sample receiving surface 403. A sample cup 801 has been placed onto the sample receiving surface 403 so that a window 802 in the bottom of the sample cup 801 reveals the sample 803 within the sample cup 801 for irradiation with the exciting X-rays. The window 802 is typically made of a thin beryllium or plastic (like polyimide or polycarbonate) foil, and has a thickness of 8–25 micrometres (beryllium) or 0.3–5 micrometres (plastic).

Even if care has been taken to ensure mechanical compatibility, it is probable that a small gap will tend to remain between the interface cassette 407 and the corresponding surface of at least one of the collimator 405, the detector 406 and the sample cup 801. All these gaps appear in FIG. 8 with their width greatly exaggerated for the sake of graphical clarity. An overpressure inside the interface cassette 407 causes the collimator side window 703, the detector side window 704 and the sample side window 705 to bulge slightly outwards, which tends to counteract the detrimental effect of said gaps: even if the surfaces of the rigid mechanical bodies remain apart from each other, the (central parts of the) windows 703, 704 and 705 press against the corresponding counterpart surfaces, driving essentially all air out from therebetween. The outwards bulging—or at least not inwards bulging—sample side window 705 also acts as a mechanical support for the sample cup window 802, which helps to keep the measurement geometry constant.

Making a window of the interface cassette match the collimator is not that important, because the absorption in air of the exciting radiation can always be compensated for by controllably increasing the intensity of exciting radiation. It is much more important to make the appropriate windows of the interface cassette match the detector and the sample (or sample cup window, or other sample holding arrangement), in order to avoid loosing fluorescent quanta through absorption and in order to eliminate stray fluorescence from the constituents of air.

Figure 9:
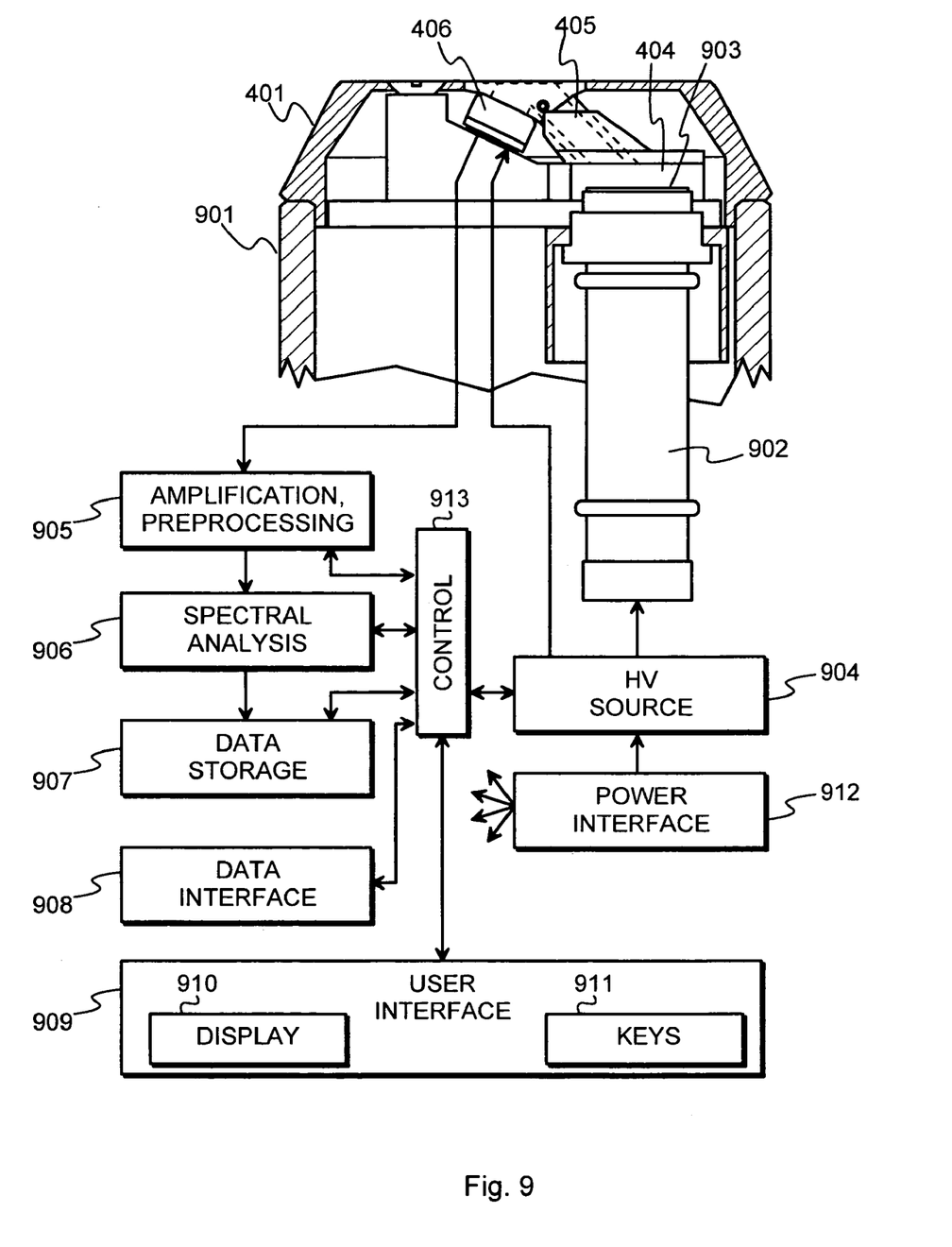
FIG. 9 illustrates a measurement apparatus according to an embodiment of the invention.

FIG. 9 illustrates schematically certain parts of a measurement apparatus according to an embodiment of the invention. A measurement head 401 is attached to a body part 901 of the measurement apparatus. An X-ray tube 902 of the end window type appears in the arrangement so that the end window 903 through which the X-rays will come is located in the place 404 for an X-ray source. The measurement apparatus comprises a high voltage source 904 adapted to provide a high voltage to the X-ray tube 902 and the detector 406, an amplification and preprocessing unit 905 adapted to receive signals from the detector 406 and to amplify and preprocess such signals, a spectral analysis unit 906 adapted to receive signals from the amplification and preprocessing unit 905 and to perform spectral analysis thereupon, and a data storage unit 907 adapted to receive and store spectral analysis data from the spectral analysis unit 906.

The structural features of the invention place few limitations to what exact wavelengths of fluorescent radiation should be detected and analysed. However, among the typical elements to be measured are aluminium, chlorine, magnesium, silicon and sulphur. The use of a gas-filled interface cassette allows measuring fluorescent radiation of these elements without a protective gas atmosphere. It is straightforward as such to select the structural and operational characteristics of the detector 406, the amplification and preprocessing unit 905, the spectral analysis unit 906 and the data storage unit so that fluorescence on the currently interesting wavelength can be measured.

Additionally the measurement apparatus comprises a data interface 908 that provides means for exchanging data with other electronic devices, and a user interface 909 that comprises displaying means 910 for displaying information and a keypad 911 for receiving key commands. The measurement apparatus also comprises a power interface 912 for receiving electric power from an external power source and for distributing electric power to the appropriate parts of the measurement apparatus. A control unit 913 is provided for controlling the operation of the measurement apparatus according to certain preprogrammed operation routines.

The end window 903 of the X-ray tube 902 is preferably made of beryllium and has a thickness between 50 and 200 micrometres. An anode layer has been formed on an inner surface of the end window 903 and comprises preferably at least one of silver, rhodium and molybdenium as a layer of 0.5–2 micrometres. Also the collimator 405 is preferably made of silver or rhodium or at least plated from the inside with a silver or rhodium layer. Some of the exciting radiation will cause fluorescence in the inner walls of the collimator 405, so if the materials are as said above, such fluorescence will sum up neatly with the original exciting radiation. Most advantageously the so-called L-line radiation of silver and/ or rhodium is used as exciting radiation, which means energies of 2.98 keV for silver and 2.70 for rhodium. For this purpose the high voltage source 904 is adapted to provide to the X-ray tube 902 an acceleration voltage the value of which is suitably high to accelerate charged particles inside the X-ray tube to speeds that are high enough to cause L-line emission when said charged particles hit the anode material.

The detector 406 may be a gas-filled detector or a semiconductor detector of a suitable type.

The apparatus of FIG. 9 does not need any integral flushing arrangements for flushing the measurement area with a gas; yet it completely avoids the harmful effects of air in X-ray fluorescence measurements with soft X-rays. Therefore a measurement apparatus according to FIG. 9 is very well suited for use as a portable measurement apparatus. At the same time the structure is easily applicable for use in compact benchtop measurement appliances.

Figure 10:
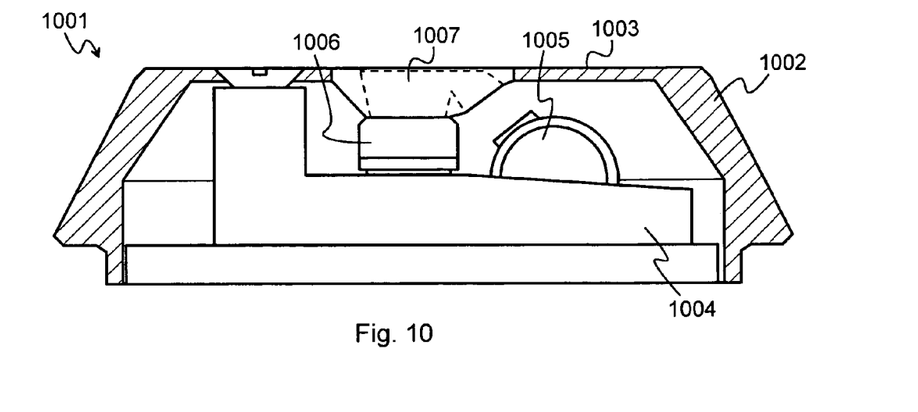
FIG. 10 illustrates a part of a measurement apparatus according to another embodiment of the invention and
FIG. 11 illustrates a part of a measurement apparatus according to yet another embodiment of the invention.

FIG. 10 illustrates an alternative structure for a measurement head in a measurement apparatus according to an embodiment of the invention. In this alternative structure the measurement head 1001 comprises an outer cover part 1002 and a sample receiving surface 1003 much like the embodiment of FIG. 4. However, the place 1004 for an X-ray source now houses an X-ray tube 1005 of the side window type, an end of which X-ray tube appears as a circle in FIG. 10. Apart from the internal structures of the X-ray tube 1005 there are no collimator means, although some could naturally be used.

The detector 1006 is now placed directly underneath the interface cassette 1007 and not at an oblique angle as in FIG. 4. A cavity inside the interface cassette 1007 has a spatial form that keeps the quanta of the exciting radiation from directly hitting the detector 1006. In this embodiment the independence of any accurate fit between the interface cassette 1007 and the source of exciting radiation is pronouncedly visible. Those properties of the interface cassette 1007 remain the same that enable accurately fitting it against the sample (or sample cup window) on one hand and against the detector 1006 on the other hand.

Figure 11:
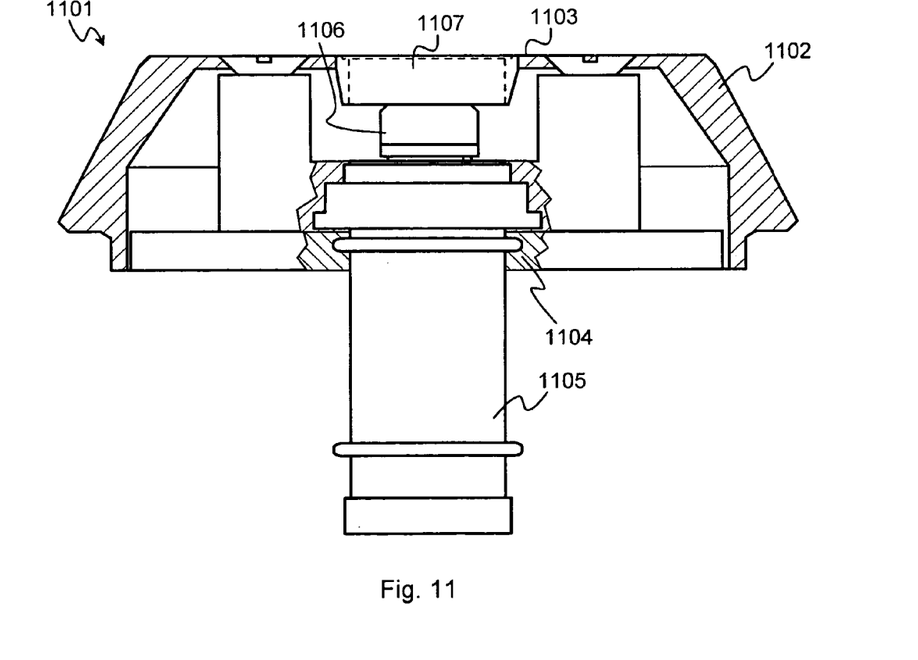

FIG. 11 illustrates another alternative structure, in which the measurement head 1101 comprises an outer cover part 1102 and a sample receiving surface 1103. The place 1104 for an X-ray source is located concentrically within the measurement head 1101, so that an X-ray tube 1105 of the end window type emits exciting radiation from directly below a sample placed against the sample receiving surface 1103. A detector 1106 is also concentrically located in the space between the X-ray tube 1105 and the sample receiving surface 1103, and appropriately shielded against X-rays coming from below. An interface cassette 1107 only needs to comprise two windows, namely a sample side window and a detector side window, of which the last-mentioned is large enough to define an outer annular region around the detector 1106 to let the exciting radiation from the X-ray tube 1105 to come in.

The invention claimed is:

1. A measurement apparatus for inducing and measuring X-ray radiation, comprising:
    an X-ray tube adapted to controllably irradiate a sample with X-rays,
    a detector adapted to detect radiation from said sample,
    a measurement head defining a sample receiving surface,
    next to said sample receiving surface, support structures defining a space for a removable separate enclosure, and
    a gas-filled separate enclosure removably fitted into said measurement head between the detector and said sample receiving surface,
wherein the measurement apparatus is a portable measurement apparatus adapted to induce and measure fluorescent X-ray radiation, and wherein said X-ray tube comprises an anode which comprises at least one of silver, rhodium and molybdenum, and wherein said X-ray tube is adapted to controllably emit L-line radiation of at least one of silver, rhodium and molybdenum.

2. A measurement apparatus according to claim 1, wherein:
    the X-ray tube is of an end window type,
    an end window of said X-ray tube is made of beryllium, has a thickness between 50 and 200 micrometers and comprises an anode layer of a thickness between 0.5 and 2 micrometers, and
    said anode layer comprises at least one of silver, rhodium and molybdenum.

3. A measurement apparatus according to claim 1, wherein the X-ray tube is of a side window type.

4. A measurement apparatus according to claim 1, comprising a collimator adapted to collimate X-rays emitted by the X-ray tube in the direction of the sample.

5. A measurement apparatus according to claim 1, comprising:
    a measurement head adapted to define a sample receiving surface, and
    a gas-filled separate enclosure between the detector and said sample receiving surface, said separate enclosure being limited by a sample side window at said sample receiving surface and a detector side window next to the detector, which sample side window and detector side window are permeable to X-rays.

6. A measurement apparatus according to claim 1, wherein:
    said separate enclosure is limited by a sample side window at a side that coincides with said sample receiving surface when said separate enclosure is within said measurement head,
    said separate enclosure is limited by a detector side window at a side that is next to the detector when said separate enclosure is within said measurement head; and
    said sample side window and detector side window are permeable to X-rays.

7. A measurement apparatus according to claim 6, wherein:
    said sample side window is made of beryllium of a thickness between 8 and 25 micrometers; or polyimide or polycarbonate of a thickness between 0.3 and 5 micrometers; and
    said detector side window is made of beryllium of a thickness between 8 and 25 micrometers.

8. A measurement apparatus according to claim 6, wherein said separate enclosure is additionally limited by an exciting radiation input window at a side that is towards the X-ray source, when said separate enclosure is within said measurement head.

9. A measurement apparatus according to claim 8, wherein said exciting radiation input window is a collimator side window at a side that is next to a collimator when said separate enclosure is within said measurement head.

10. A measurement apparatus according to claim 8, wherein said exciting radiation input window is made of beryllium of a thickness between 8 and 50 micrometers.

11. A measurement apparatus according to claim 6, wherein said separate enclosure contains gas having a pressure that is higher than ambient pressure around said measurement head.

12. A measurement apparatus according to claim 11, wherein said separate enclosure comprises a filling valve for enabling controlling the pressure of said gas.

13. A measurement apparatus according to claim 1, wherein the portable measurement apparatus also comprises a sample cap for holding volatile liquid as a sample, which sample cup has a window at a bottom of said sample cup, which window is adapted to be supported by a part of said separate enclosure when said sample cup is placed on top of a measurement head having said separate enclosure installed therein.

14. A measurement apparatus according to claim 1, comprising a protective window adapted to cover an opening in said sample receiving surface, when said measurement head does not have said separate enclosure installed therein.

15. A measurement apparatus according to claim 1, wherein:
    the measurement apparatus comprises a measurement head adapted to define a sample receiving surface;
    a direction of exciting X-rays passing between the X-ray source and a sample placed against said sample receiving surface is at an oblique angle against said sample receiving surface, and a direction of fluorescent X-rays passing between a sample placed against said sample receiving surface and the detector is at an oblique angle against said sample receiving surface.

16. A measurement apparatus according to claim 1, wherein:
the measurement apparatus comprises a measurement head adapted to define a sample receiving surface,
a direction of exciting X-rays passing between the X-ray source and a sample placed against said sample receiving surface is at an oblique angle against said sample receiving surface, and
a direction of fluorescent X-rays passing between a sample placed against said sample receiving surface and the detector is at a right angle against said sample receiving surface.

17. A measurement apparatus according to claim 1, wherein the detector is a detector adapted to detect fluorescent radiation of at least one of aluminum, chlorine, magnesium, silicon, and sulphur.

18. An interface cassette for setting up an interface between parts in an X-ray fluorescence measurement apparatus, comprising:
a body part, which defines a cavity therein and an outside form for removably attaching the interface cassette to the X-ray fluorescence measurement apparatus,
a sample side window between said cavity and the outside of the interface cassette and
a detector side window between said cavity and the outside of the interface cassette, wherein said sample side window and said detector side window are permeable to X-rays.

19. An interface cassette according to claim 18, wherein:
said sample side window is made of berrylium of a thickness between 8 and 25 micrometers; or polyimide or polycarbonate of a thickness between 0.3 and 5 micrometers; and
said detector side window is made of berrylium of a thickness between 8 and 25 micrometers.

20. An interface cassette according to claim 18, comprising an exciting radiation input window at a side that is towards an X-ray source, when said interface cassette is within a measurement head of the X-ray fluorescence measurement apparatus.

21. An interface cassette according to claim 18, wherein said exciting radiation input window is made of berrylium of a thickness between 8 and 50 micrometers.

22. An interface cassette according to claim 18, wherein the interface cassette contains gas in said cavity, said gas having a pressure that is higher than ambient pressure around said interface cassette.

23. An interface cassette according to claim 22, comprising a filling valve to control the pressure of said gas.

* * * * *